(12) United States Patent
Miyata et al.

(10) Patent No.: US 7,183,322 B2
(45) Date of Patent: Feb. 27, 2007

(54) REMEDY FOR HYPERTENSION

(75) Inventors: Noriyuki Miyata, Tokyo (JP); Shigeru Okuyama, Tokyo (JP); Teisuke Takahashi, Tokyo (JP); Kenzo Takahashi, Tokyo (JP)

(73) Assignee: Taisho Pharmaceutical Co., Ltd., Tokyo (JP)

( * ) Notice: Subject to any disclaimer, the term of this patent is extended or adjusted under 35 U.S.C. 154(b) by 0 days.

(21) Appl. No.: 10/504,585

(22) PCT Filed: Feb. 17, 2003

(86) PCT No.: PCT/JP03/01625

§ 371 (c)(1),
(2), (4) Date: May 4, 2005

(87) PCT Pub. No.: WO03/068263

PCT Pub. Date: Aug. 21, 2003

(65) Prior Publication Data

US 2005/0222268 A1      Oct. 6, 2005

(30) Foreign Application Priority Data

Feb. 15, 2002   (JP) ............................ 2002-039008

(51) Int. Cl.
*A61K 31/135* (2006.01)
(52) U.S. Cl. .................................................. 514/646
(58) Field of Classification Search .................. None
See application file for complete search history.

(56) References Cited

U.S. PATENT DOCUMENTS

| | | | | |
|---|---|---|---|---|
| 6,156,801 A | * | 12/2000 | Ota et al. ................... | 514/646 |
| 6,162,832 A | * | 12/2000 | Ota et al. ................... | 514/646 |
| 6,423,705 B1 | * | 7/2002 | Tracey et al. ............... | 514/221 |
| 2002/0082193 A1 | * | 6/2002 | Anderson et al. ........... | 514/1 |

FOREIGN PATENT DOCUMENTS

| | | | |
|---|---|---|---|
| JP | 2002-233376 A | | 8/2002 |
| WO | WO98/43943 | * | 10/1998 |
| WO | WO99/20598 | * | 4/1999 |

OTHER PUBLICATIONS

Medline Accession No. 95067100, an abstract of Kashiwagi et al., Acta neurochirurgica, Supplementum, (1994), vol. 60, pp. 289-292.*
Biosis Accession No. 2001:285417, an abstract of Yamashita et al., Journal of Pharmacology and Experimental Therapeutics, (Feb., 2001), vol. 286, No. 2, pp. 412-419.*
Cecil Textbook of Medicine, 21st Edition, vol. 1, published 2000 by W.B.Saunders Company (PA), pp. 258-273.*
Yamashita, Junji, et al., "Pre- or Post—Ischemic Treatment with a Novel $Na^+/Ca^{2+}$ Exchange Inhibitor, KB-R7943, Shows Renal Protective Effects in Rats with Ischemic Acute Renal Failure", *The Journal of Pharmacology and Experimental Therapeutics*, Feb., 2001, vol. 296, No. 2, pp. 412-419.
Kashiwagi, F. et al., "Effects of a new calcium antagonist (SM-6586) on experimental cerebral ischemia.", *Acta. Neurorirurgica*. Supplementum, 1994, vol. 60, pp. 289-292 (abstract) Medline [online]: Retrieved from STN, Medline Accession No. 95067100.
Yamashita, Junji, et al., "Pre- or Post—Ischemic Treatment with a Novel $Na^+/Ca^{2+}$ Exchange Inhibitor, KB-R7943, Shows Renal Protective Effects in Rats with Ischemic Acute Failure", *The Journal of Pharmacology and Experimental Therapeutics*, Feb., 2001, vol. 296, No. 2, pp. 412-419.
Kashiwagi, F. et al., "Effects of a new calcium antagonist (SM-6586) on experimental cerebral ischemia.", *Acta. Neurorirurgica*. Supplementum, 1994, vol. 60, pp. 289-292 (Full Article Considered).
Kashiwagi, F. et al., "Effects of a new calcium antagonist (SM-6586) on experimental cerebral ischemia.", *Acta. Neurorirurgica*. Supplementum, 1994, vol. 60, pp. 289-292 (abstract) Medline [online]: Retrieved from STN, Medline Accession No. 95067100.

* cited by examiner

*Primary Examiner*—Raymond J. Henley, III
(74) *Attorney, Agent, or Firm*—Sughrue Mion, PLLC

(57) ABSTRACT

A therapeutic agent for hypertension, which comprises as an active ingredient a compound capable of inhibiting $Na^+/Ca^{2+}$ exchanger 1.

3 Claims, No Drawings

REMEDY FOR HYPERTENSION

This is a National Stage Application of Application No. PCT/JP03/01625 filed Feb. 17, 2003; the disclosure of which is incorporated herein by reference.

TECHNICAL FIELD

The present invention relates to novel therapeutic agents for hypertension.

BACKGROUND ART

Intracellular free $Ca^{2+}$ is an important ion for controlling the contraction of cardiac muscle and various smooth muscles, the release of neurotransmitters, and the expression of genes. The concentration of such $Ca^{2+}$ ion is regulated by $Ca^{2+}$ pumps, $Ca^{2+}$ channels and/or $Na^+/Ca^{2+}$ exchangers (NCX) present in the plasma membrane and the sarcoplasmic reticulum membrane. Among them, $Na^+/Ca^{2+}$ exchangers play a particularly important role in the contraction and relaxation of cardiac muscle and vascular smooth muscle (Ann. Rev. Physiol., vol. 52, p. 467 (1990)). At present, three NCX genes have been isolated and identified from mammals. Moreover, it is known that NCX1 protein is expressed at high levels in the brain, heart and kidney, NCX2 protein is expressed primarily in the brain and also expressed, but slightly, in visceral smooth muscle, and NCX3 protein is expressed primarily in the brain and also expressed, but slightly, in skeletal muscle (Jpn. J. Circ. Res, vol. 24, no. 3, p. 101 (2001); Am. J. Physiol., 272, C1250–C1261 (1997)).

As for NCX inhibitors, isothiourea derivatives such as 2-[2-[4-[nitrobenzyloxy]phenyl] ethyl]isothio-ureamethanesulfonate (K-BR7943) and phenoxyaniline derivatives such as 2-[4-[(2,5-difluorophenyl)methoxy]phenoxy]-5-ethoxyaniline (SEA0400) have been reported, and K-BR7943 has been confirmed to have efficacy in acute mycardial infarction models as well as brain and kidney ischemia/reperfusion models (J. Pharmacol. Exp. Ther., vol. 296, p. 412 (2001)). However, there is no report about the application of NCX inhibitors as therapeutic agents for hypertension.

DISCLOSURE OF THE INVENTION

The inventors of the present invention investigated the NCX-inhibiting activity of K-BR7943, SEA0400 and other compounds by using $Na^+/Ca^{2+}$ exchangers (NCX) prepared from brain, heart and kidney. As a result, it has been found that phenoxyaniline derivatives (including SEA0400) and phenoxypyridine derivatives selectively inhibit NCX derived from the heart and kidney, as compared with NCX derived from brain tissue.

In addition, previous studies have reported that the above-mentioned compounds had little effect on other receptors, channels and transporters, at a concentration sufficient to inhibit NCX (J. Pharmacol. Exp. Ther., vol. 298, p. 249 (2001)).

In view of the foregoing, phenoxyaniline derivatives and the like are found to have high selectivity for NCX1.

With the aim of elucidating the relationship between NCX1 and diseases or their treatment, the inventors of the present invention made further investigation in various disease models (e.g., diabetic rats, salt-sensitive hypertension models) using the above NCX1-selective inhibitors. As a result, it has been found that inhibition of NCX1 is effective in reducing the blood pressure in salt-sensitive hypertension models. These findings led to the completion of the present invention.

Namely, the present invention is directed to a therapeutic agent for hypertension, which comprises as an active ingredient a compound capable of inhibiting $Na^+/Ca^{2+}$ exchanger 1.

Further, the present invention is directed to a therapeutic agent for hypertension, which comprises as an active ingredient a 2-phenoxyaniline derivative of Formula (1):

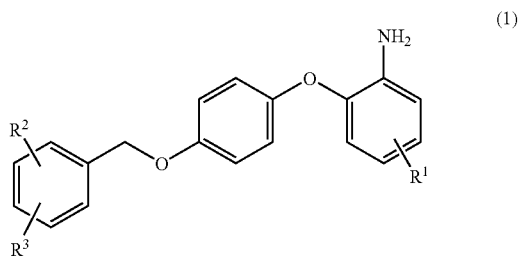

(1)

wherein $R^1$ represents a hydrogen atom or a $C_1$–$C_6$ alkoxy group, $R^2$ represents a halogen atom or a nitro group, and $R^3$ represents a hydrogen atom or a halogen atom; or a pharmaceutically acceptable salt thereof.

BEST MODE FOR CARRYING OUT THE INVENTION

In the present invention, NCX1 inhibiting compounds are not limited as long as they inhibit kidney-derived NCX1, preferred are those which produce greater than 50% inhibition at a concentration of 3 µM when assayed by the test described later (Reference Example 3). In terms of avoiding side effects, more preferred are compounds capable of specifically inhibiting NCX1.

The compound capable of specifically inhibiting NCX1 means a compound that does not substantially inhibit other receptors, channels and transporters at a concentration sufficient to inhibit NCX 1. More specifically, for example, when used at a concentration of 3 µM, such a compound preferably does not cause greater than 50% inhibition of $Ca^{2+}$ channels, $Na^+$ channels, $K^+$ channels, $Na^+/H^+$ transporters, norepinephrine transporters, $Na^+$, $K^+$-ATPase, $Ca^{2+}$-ATPase, phospholipase $A_2$, phospholipase C, 5-lipoxygenase, inducible nitric-oxide synthetase, constitutive nitric-oxide synthetase, Adenosine receptors, Adrenergic receptors, Glutamate receptors, Bradykinin receptors, LTB4 receptors or PAF receptors. It should be noted that procedures for measurement using these individual ion channels, enzymes and receptors are disclosed in J. Pharmacol. Exp. Ther., vol. 298, p. 249 (2001) and references cited therein.

Examples of the compound capable of specifically inhibiting NCX1 include phenoxyaniline derivatives and phenoxypyridine derivatives.

Preferred are compounds of Formula (2):

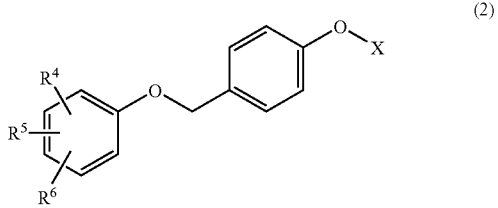

wherein $R^4$, $R^5$ and $R^6$, which may be identical or different, each represent a hydrogen atom or a halogen atom, X represents:

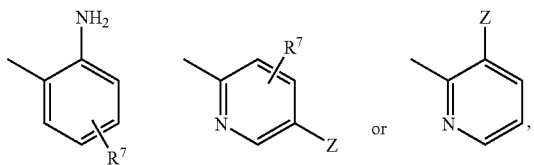

$R^7$ represents a hydrogen atom, a substituted or unsubstituted $C_1$–$C_6$ alkyl group or a substituted or unsubstituted $C_1$–$C_6$ alkoxy group, Z represents a nitro group, an amino group or a $NHC(O)CH_2R^8$ group, $R^8$ represents a hydrogen atom, a substituted or unsubstituted $C_1$–$C_6$ alkyl group, a substituted or unsubstituted $C_1$–$C_6$ alkoxy group, a halogen atom, a hydroxy group, a $C_2$–$C_7$ acyloxy group, $NR^9R^{10}$ or

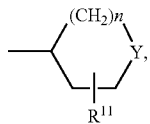

$R^9$ and $R^{10}$, which may be identical or different, each represent a hydrogen atom, a substituted or unsubstituted $C_1$–$C_6$ alkyl group or an N-methyl-4-piperidinyl group, $R^{11}$ represents a hydrogen atom, a hydroxy group or a $C_2$–$C_7$ alkoxycarbonyl group, Y represents a methylene group, an epoxy group, a thio group or a $NR^{12}$ group, n represents an integer of 1 to 4, and $R^{12}$ represents a hydrogen atom, a substituted or unsubstituted $C_1$–$C_6$ alkyl group or a substituted or unsubstituted phenyl group; or a pharmaceutically acceptable salt thereof.

In terms of NCX1-inhibiting activity, more preferred are 2-phenoxyaniline derivatives of Formula (1):

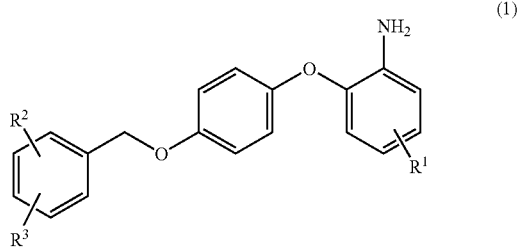

wherein $R^1$ represents a hydrogen atom or a $C_1$–$C_6$ alkoxy group, $R^2$ represents a halogen atom or a nitro group, and $R^3$ represents a hydrogen atom or a halogen atom; or a pharmaceutically acceptable salt thereof.

In Formulae (1) and (2), a $C_1$–$C_6$ alkoxy group means a linear or branched alkoxy group containing 1 to 6 carbon atoms. Examples include a methoxy group, an ethoxy group, a propoxy group, an isopropoxy group, a butoxy group, an isobutoxy group, a sec-butoxy group, a tert-butoxy group, a pentyloxy group, an isopentyloxy group, a neopentyloxy group, a tert-pentyloxy group, a 1-methylbutoxy group, a 2-methylbutoxy group, a 1,2-dimethylpropoxy group, a hexyloxy group and an isohexyloxy group.

Examples of a substituent for the substituted $C_1$–$C_6$ alkoxy group include a chloro group, a fluoro group, a nitro group, an amino group, a dimethylamino group, a carboxyl group, a methoxycarbonyl group, an ethoxycarbonyl group, a phenyl group, a hydroxy group, a cyano group and a carbamoyl group.

A halogen atom refers to a fluorine atom, a chlorine atom, a bromine atom or an iodine atom.

A $C_1$–$C_6$ alkyl group means a linear or branched alkyl group containing 1 to 6 carbon atoms. Examples include a methyl group, an ethyl group, a propyl group, an isopropyl group, a butyl group, an isobutyl group, a sec-butyl group, a tert-butyl group, a pentyl group, an isopentyl group, a neopentyl group, a tert-pentyl group, a 1-methylbutyl group, a 2-methylbutyl group, a 1,2-dimethylpropyl group, a hexyl group and an isohexyl group.

Examples of a substituent for the substituted $C_1$–$C_6$ alkyl group include a chloro group, a fluoro group, a nitro group, an amino group, a dimethylamino group, a carboxyl group, a methoxycarbonyl group, an ethoxycarbonyl group, a phenyl group, a methoxy group, an ethoxy group, a hydroxy group, a cyano group and a carbamoyl group.

A $C_2$–$C_7$ acyloxy group means a linear or branched acyloxy group containing 2 to 7 carbon atoms, whose acyl moiety may be cyclic or may contain an aromatic group. Examples include an acetoxy group, a propionyloxy group, an isopropionyloxy group, a cyclohexyloxy group and a benzoyloxy group.

A $C_2$–$C_7$ alkoxycarbonyl group means a linear or branched alkoxycarbonyl group containing 2 to 7 carbon atoms, whose alkoxyl moiety may be cyclic or may contain an aromatic group. Examples include a methoxycarbonyl group, an ethoxycarbonyl group, a propoxycarbonyl group, an isopropoxycarbonyl group, a butoxycarbonyl group, an isobutoxycarbonyl group, a sec-butoxycarbonyl group, a tert-butoxycarbonyl group, a pentyloxycarbonyl group, an isopentyloxycarbonyl group, a neopentyloxycarbonyl group, a tert-pentyloxycarbonyl group, a 1-methylbutoxycarbonyl group, a 2-methylbutoxycarbonyl group, a 1,2-dimethylpropoxycarbonyl group, a hexyloxycarbonyl group and an isohexyloxycarbonyl group.

Examples of a substituent for the substituted phenyl group include a chloro group, a fluoro group, a nitro group, an amino group, a dimethylamino group, a carboxyl group, a methoxycarbonyl group, an ethoxycarbonyl group, a methyl group, an ethyl group, a methoxy group, an ethoxy group, a hydroxy group, a cyano group and a carbamoyl group.

Examples of compounds having an excellent activity for hypertension are the compound shown below (SEA0400)

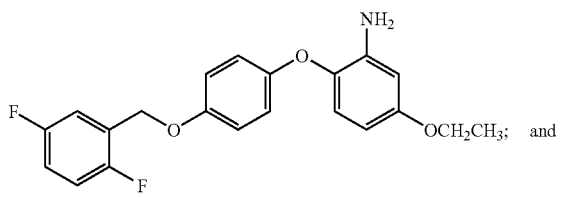

and the compound shown below (SEA0064).

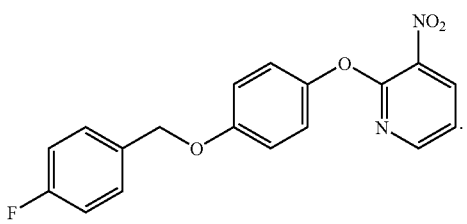

Moreover, to avoid side effects, such compounds preferably produce stronger inhibition on NCX1 than on NCX2 and NCX3. For example, the compounds that have smaller values of $IC_{50}$ (renal cortex-derived)/$IC_{50}$ (brain-derived), and $IC_{50}$ (renal cortex-derived)/$IC_{50}$ (cardiac sarcolemma-derived) when measured as described later, than SEA 0400 are preferred.

It should be noted that the compounds of Formulae (1) and (2) can be synthesized according to the procedures as described in WO98/43943, WO99/20598, Japanese Laid-Open Patent Hei 10-265460, Japanese Laid-Open Patent Hei 10-218844, Japanese Laid-Open Patent Hei 11-49752 and Japanese Laid-Open Patent Hei 11-92454.

As used herein, the therapeutic agent for a hypertension is intended to mean a therapeutic agent for salt-sensitive hypertension, renal hypertension, essential hypertension, gestational hypertension or primary aldosteronism.

The therapeutic agent of the present invention can be prepared as a pharmaceutical composition in any desired dosage form for oral or parenteral use (e.g., tablets, pills, capsules, granules, dry syrups, injectable preparations), in combination with known carriers, diluents and so on, as appropriate.

Solid preparations can be prepared by stirring granulation, fluidized-bed granulation or milling granulation using various additives such as excipients, disintegrating agents, binders, lubricants and coating bases.

If necessary, it is also possible to add other additives such as antioxidants, coating agents, coloring agents, flavoring agents, surfactants and plasticizers.

The dose of the active ingredient in the pharmaceutical preparation of the present invention will vary depending on age, body weight, dosage form, and so on, but the usual dose to an adult is 0.1 to 1000 mg/day, which can be administrated once or several times a day.

The present invention will now be described with reference to the following Formulation Examples and Test Examples, which are not intended to limit the scope of the invention.

FORMULATION EXAMPLE 1

| | |
|---|---|
| SEA0400 | 50 mg |
| Lactose | 40 mg |
| Corn starch | 49.75 mg |
| Crystalline cellulose | 17 mg |
| Carmellose calcium | 17 mg |
| Hydroxypropylcellulose | 5.25 mg |
| Magnesium stearate | 1 mg |
| Total | 180 mg |

SEA0400, lactose, corn starch, crystalline cellulose and carmellose calcium were mixed uniformly, followed by addition of a 10% aqueous hydroxypropylcellulose solution. After kneading and drying, the resulting granules were passed through a 30M sieve to give uniform granules, which were then supplemented with magnesium stearate and tabletted into tablets.

FORMULATION EXAMPLE 2

| | |
|---|---|
| SEA0064 | 50 mg |
| Lactose | 40 mg |
| Corn starch | 49.75 mg |
| Crystalline cellulose | 17 mg |
| Carmellose calcium | 17 mg |
| Hydroxypropylcellulose | 5.25 mg |
| Magnesium stearate | 1 mg |
| Total | 180 mg |

SEA0064, lactose, corn starch, crystalline cellulose and carmellose calcium were mixed uniformly, followed by addition of a 10% aqueous hydroxypropylcellulose solution. After kneading and drying, the resulting granules were passed through a 30M sieve to give uniform granules, which were then supplemented with magnesium stearate and tabletted into tablets.

Reference Example 1

Method of Measuring for Brain Microsomal $Na^+/Ca^{2+}$ Exchanger

Brain microsomes (1.5 mg/ml) obtained from 8-week-old rats were pre-treated with 160 mM NaCl-containing buffer to cause Na loading into membrane vesicles. This suspension was diluted 50-fold with 20 μM $^{45}CaCl_2$-containing buffer to induce $^{45}Ca$ uptake, followed by dilution with the buffer (0° C.) to stop the reaction. The membrane vesicles were immediately collected on a nitrocellulose filter. Subsequently, $^{45}Ca$ trapped inside the membrane vesicles was determined by liquid scintillation counting. The above assay for $Na^+/Ca^{2+}$ exchange activity in brain microsomes was performed according to the procedures described in J. Biol. Chem., vol. 257, p. 5111 (1982).

Reference Example 2

Method of Measuring for Canine Cardiac Sarcolemmal Vesicle $Na^+/Ca^{2+}$ Exchanger Canine cardiac sarcolemmal vesicles (0.5 mg/ml) were prepared by centrifugal fractionation as described in Methods enzymology, vol. 157, p. 85 (1988) and suspended in Solution A (20 mM MOPS-Tris (pH 7.4), 160 mM NaCl or KCl), followed by incubation at room temperature for about one hour to cause Na or K loading into the vesicles. This suspension was diluted 50-fold with 20 µM $^{45}CaCl_2$-containing buffer to induce $^{45}Ca$ uptake, followed by dilution with the buffer (0° C.) to stop the reaction. The membrane vesicles were immediately collected on a nitrocellulose filter. Subsequently, $^{45}Ca$ trapped inside the membrane vesicles was determined by liquid scintillation counting. The $Na^+/Ca^{2+}$ exchange activity was evaluated by subtracting the value obtained for K loading from the value obtained for Na loading. The above assay for $Na^+/Ca^{2+}$ exchange activity in canine cardiac sarcolemmal vesicles was performed according to the procedures described in J. Biol. Chem., vol. 257, p. 5111 (1982).

Reference Example 3

Preparation of Rat Renal Cortex-derived BLMVs (Basolateral Membrane Vesicles) and Method of Measuring for their $Na^+/Ca^{2+}$ Exchange Activity (Preparation of BLMVs)

BLMVs were prepared from rat renal cortex and assayed for $Na^+/Ca^{2+}$ exchange activity according to the procedures described in Am. J. Physiol., vol. 266, p. F785 (1994).

After being excised from rats, the kidneys were placed in ice-cold sucrose buffer (0.25 mM sucrose, 0.1 mM PMSF, 10 mM Tris-HCl (pH 7.6)) and decapsulated. The isolated cortex was then finely minced in the sucrose buffer and homogenized sequentially with a Dounce-type homogenizer and a Polytron-type homogenizer, followed by centrifugation at 2500 g for 15 minutes to collect the supernatant. Centrifugation was repeated at 24000 g for 20 minutes to collect the white fluffy portion of the pellet. After further addition of the sucrose buffer, the collected fraction was homogenized with a Dounce-type homogenizer, supplemented with Percoll and then centrifuged at 30000 g for 35 minutes to collect the middle layer. After addition of buffer (100 mM KCl, 100 mM mannitol, 5 mM HEPES-Tris (pH 7.4)), centrifugation was carried out at 34000 g for 30 minutes to collect the loose white pellet (BLMVs). The pellet was further suspended in the KCl-mannitol buffer and then centrifuged at 34000 g for 30 minutes to collect the precipitate, which was used for activity assay.

(Method of Measuring for $Na^+/Ca^{2+}$ Exchanger (Na-dependent $^{45}Ca$ Uptake))

The BLMVs thus prepared were equilibrated at 37° C. for 10 minutes in pre-equilibration buffer (100 mM NaCl, 40 mM KCl, 1 mM $MgSO_4$, 10 mM glucose, 5 mM HEPES-Tris (pH 7.4)) and then centrifuged at 20000 g for 5 minutes to collect the precipitate, which was then resuspended in the pre-equilibration buffer. Centrifugation was repeated to collect the precipitate, followed by resuspension in the pre-equilibration buffer. The resulting BLMV suspension was diluted 20-fold with external medium (100 mM choline chloride, 40 mM KCl, 1 mM $MgSO_4$, 10 mM glucose, 5 mM HEPES-Tris (pH 7.4), 25 µM valinomycin, 10 µM $CaCl_2$, 1 mCi/l $^{45}CaCl_2$) to start uptake. After reaction at 25° C. for a given period of time, 2 ml stop solution (ice-cold 150 mM KCl) was added to stop the reaction, and the reaction mixture was immediately filtered through an ultrafiltration membrane (0.45 µm nitrocellulose filter) to collect BLMVs on the filter. Subsequently, the filter was washed twice with 2 ml stop solution and then the amount of $^{45}Ca$ trapped inside the BLMVs was determined by using liquid scintillation method.

TABLE 1

| | Inhibitory activity against $Na^+/Ca^{2+}$ exchange (Na-dependent $^{45}Ca$ uptake) | | |
|---|---|---|---|
| | Brain | Cardiac sarcolemma | ($IC_{50}$ value: µM) Renal cortex |
| K-BR7943 | 11.0 | 7.0 | 6.8 |
| SEA0400 | 0.2 | 0.09 | 0.02 |

Likewise, SEA0064 was also confirmed to show an inhibitory activity of about 0.07-fold of SEA0400, by measuring for renal cortex-derived $Na^+/Ca^{2+}$ exchange activity.

Test Example 1

<Method>

(Creation of Dahl Salt-sensitive Hypertension Rat Model)

Dahl salt-sensitive hypertension rats (7 weeks old) were used in the experiment. They were fed a 4% NaCl high-salt chow (0.6% for normal chow), but were allowed to drink water without any restriction. At two weeks after high-salt loading, the animals confirmed to develop hypertension were divided into the following 4 groups for use in the experiment.

(Experimental Animal Groups)

| Group I: | solvent (20% fat emulsion) |
|---|---|
| Group II: | SEA0400  3 mg/kg |
| Group III: | SEA0400  10 mg/kg |
| Group IV: | SEA0400  30 mg/kg |

(Experimental Schedule)

After loading the high-salt chow for two weeks as described above, an acute experiment was performed. On the day of the experiment, the systolic blood pressure (before administration) was measured for each animal under non-anesthesia conditions using a noninvasive sphygmomanometer. The animals were then administered orally with the solvent or SEA0400(3, 10, or 30 mg/kg) and monitored over time for their systolic blood pressure.

(Result)

The level of systolic blood pressure before administration was 140±3, 148±4, 143±3 and 142±4 mmHg in Group I, II, III and IV, respectively. The % change in blood pressure at one hour after administration was −3.8±1.0% in the solvent group, −9.5±1.8% in the SEA0400 3 mg/kg group, −12.0±0.9% in the SEA0400 10 mg/kg group and −12.7±3.4% in the SEA0400 30 mg/kg group. When compared with the solvent group, the 10 mg/kg and 30 mg/kg SEA 0400 group both showed a significant reduction in blood pressure.

INDUSTRIAL APPLICABILITY

The present invention enables to provide therapeutic agents for hypertension that are based on a novel mechanism of action. They are useful for treating and preventing hypertension with fewer side effects.

What is claimed is:

1. A method for treating hypertension consisting of administering to a subject in need of treatment a therapeutically effective amount of a composition wherein an active ingredient consists of a compound that inhibits $Na^+/Ca^{2+}$ exchanger 1 (NCX-1).

2. The method of claim 1, wherein the compound that inhibits NCX-1 is a compound of Formula (1):

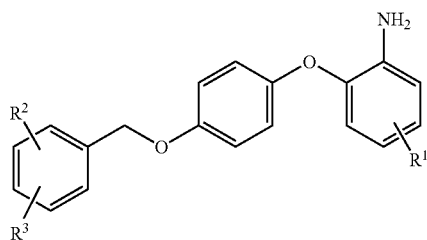
(1)

wherein $R^1$ represents a hydrogen atom or a $C_1$–$C_6$ alkoxy group, $R^2$ represents a halogen atom or a nitro group, and $R^3$ represents a hydrogen atom or a halogen atom; or a pharmaceutically acceptable salt thereof.

3. The method of claim 1, wherein the compound that inhibits NCX-1 is the following compound:

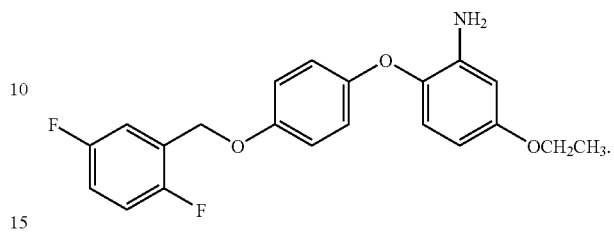

\* \* \* \* \*